(12) United States Patent
Anelli et al.

(10) Patent No.: US 9,289,555 B2
(45) Date of Patent: Mar. 22, 2016

(54) FINGER-GRIP DEVICE FOR MEDICAL SYRINGE OR CARTRIDGE

(75) Inventors: Pier Lucio Anelli, Milan (IT); Mauro Citterio, Merate (IT); Paolo Morosi, Turate (IT)

(73) Assignee: BRACCO IMAGING S.P.A., Milan (IT)

( * ) Notice: Subject to any disclaimer, the term of this patent is extended or adjusted under 35 U.S.C. 154(b) by 110 days.

(21) Appl. No.: 13/825,862

(22) PCT Filed: Sep. 29, 2011

(86) PCT No.: PCT/EP2011/066958
§ 371 (c)(1),
(2), (4) Date: Mar. 25, 2013

(87) PCT Pub. No.: WO2012/041946
PCT Pub. Date: Apr. 5, 2012

(65) Prior Publication Data
US 2013/0178737 A1 Jul. 11, 2013

(30) Foreign Application Priority Data
Oct. 1, 2010 (IT) .............. MI2010A1800

(51) Int. Cl.
*A61M 5/315* (2006.01)
*A61M 5/31* (2006.01)
*A61M 5/00* (2006.01)

(52) U.S. Cl.
CPC ............. *A61M 5/3137* (2013.01); *A61M 5/007* (2013.01); *A61M 2005/3139* (2013.01)

(58) Field of Classification Search
CPC ................. A61M 2005/3139; A61M 5/007; A61M 5/3137
USPC ................... 604/220–222, 227, 187
See application file for complete search history.

(56) References Cited

U.S. PATENT DOCUMENTS

| | | | |
|---|---|---|---|
| 5,667,495 A * | 9/1997 | Bitdinger et al. | ............ 604/220 |
| 5,700,247 A | 12/1997 | Grimard et al. | |
| 5,803,918 A | 9/1998 | Vetter et al. | |
| 5,997,514 A | 12/1999 | Balestracci | |
| 6,004,299 A | 12/1999 | Arai et al. | |
| 7,488,307 B2 | 2/2009 | Rimlinger et al. | |
| 7,875,007 B2 | 1/2011 | Perot et al. | |
| 7,951,120 B2 | 5/2011 | Wolbring et al. | |

(Continued)

FOREIGN PATENT DOCUMENTS

| | | |
|---|---|---|
| DE | 19613035 A1 | 9/1997 |
| DE | 102005005468 A1 | 8/2006 |

(Continued)

OTHER PUBLICATIONS

PCT international Search Report for PCT/EP2011/066958, mail date Feb. 3, 2012.

(Continued)

*Primary Examiner* — Rebecca E Eisenberg
(74) *Attorney, Agent, or Firm* — Vivicar Law, PLLC (57) ABSTRACT

The present invention relates to a finger-grip device designed to be placed on the flange of a cylindrical barrel of a medical syringe or cartridge, increasing the contact surface with the fingers of the operator during the injection or withdrawal of fluids to or from a patient, characterised in that it does not stop or hinder the run of the plunger within the cylindrical barrel.

19 Claims, 7 Drawing Sheets

(56) References Cited

U.S. PATENT DOCUMENTS

| | | |
|---|---|---|
| 8,016,795 B2 | 9/2011 | Barrelle et al. |
| 8,240,511 B2 | 8/2012 | Greter et al. |
| 2003/0220615 A1 | 11/2003 | Fabian et al. |
| 2004/0034323 A1 | 2/2004 | Manthey |
| 2004/0116875 A1 | 6/2004 | Fischer et al. |
| 2007/0083164 A1 | 4/2007 | Barrelle et al. |
| 2008/0188799 A1 | 8/2008 | Mueller-Beckhaus et al. |
| 2010/0249713 A1* | 9/2010 | Burkholz ............... 604/177 |

FOREIGN PATENT DOCUMENTS

| | | |
|---|---|---|
| EP | 0738517 A1 | 10/1996 |
| EP | 0792659 A2 | 9/1997 |
| FR | 2830199 A1 | 4/2003 |
| JP | 4400112 B2 | 1/2010 |
| WO | 2010111285 A1 | 9/2010 |

OTHER PUBLICATIONS

PCT Written Opinion for PCT/EP2011/066958, mail date Feb. 3, 2012.
Invitation for Amendment for Japanese application No. 2013-600056, mail date Aug. 27, 2013 (English translation).
Office Action for Australian application No. 2011310580, mail date Jan. 3, 2014.
PCT International Preliminary Report on Patentability for PCT/EP2011/066958, mail date Apr. 11, 2013.
Office Action for Australian application No. 2011310580, mail date Sep. 30, 2015.
Office Action for Canadian application No. 2,813,060, mail date Jul. 10, 2015.

* cited by examiner

FINGER-GRIP DEVICE FOR MEDICAL SYRINGE OR CARTRIDGE

CROSS-REFERENCE TO RELATED APPLICATIONS

This application is the national stage application of corresponding international application number PCT/EP2011/066958 filed Sep. 29, 2011, which claims priority to and the benefit of Italian application no. MI2010A001800, filed Oct. 1, 2010, all of which are hereby incorporated by reference in their entirety.

FIELD OF THE INVENTION

The present invention relates to a finger-grip device designed to be placed on the flange of the cylindrical barrel of a medical syringe or cartridge, useful to increase the contact surface with the fingers of the operator during the injection or withdrawal of fluids to or from a patient.

STATE OF THE ART

Different types of syringes and cartridges used in medicine for the administration or withdrawal of fluids are well known in the art and they have achieved high quality standards both in terms of configuration and materials. Generally, these syringes are made of glass and/or polymeric materials, and their main functional parts are:
1. a cylindrical barrel, and
2. a plunger configured to slide inside said cylindrical barrel.

The plunger may optionally present a plunger-rod, which in its turn can be removably or permanently attached to the plunger. The cylindrical barrel, on the other hand, presents a terminal side into which it is inserted the plunger, and a distal side configured in such a way that a needle or a canula may be connected thereto. The cylindrical barrel typically contains a certain amount of a chosen fluid, whereas a pressure of the plunger toward the distal side of the barrel causes the fluid leakage. Similarly, when the syringe is used for the withdrawal of fluids, e.g. from a patient, the plunger, being positioned close to the distal side of the cylindrical barrel, is pulled toward the terminal side of the cylinder, thus causing the aspiration of the fluid inside the cylindrical barrel. When the plunger is inserted into the barrel, the plunger dimensions are such that a suitable adherence is created between such two means, in order, e.g., to avoid the collateral outflow of the fluid either during the operations of administration or withdrawal.

In particular, it has to be noted that during said operations, the operator should face two types of forces: the so called "breakaway force" and the "running force". The former is the force at the beginning of the injection or withdrawal operation, required to move on the plunger from its initial position, whilst the latter refers to the force required to maintain the run of the plunger (and therefore the rate of injection or withdrawal) as constant and smooth as possible.

As well known, the syringe is typically handled by using a single hand only, and accordingly the syringe should be provided with a contact surface, generally for the index finger and middle finger, which, e.g. during an operation of injection, allows to apply a certain required pressure to the plunger typically by means of the thumb. To this purpose, some finger-grip devices are known in the art, suitably designed to enhance said contact surface. Such devices usually apply to the cylindrical barrel of a syringe, or a cartridge, and they have different shapes and features, depending for instance on the frame of the barrel. This latter, in fact, may present a flange having different sizes and shapes at its terminal side, or it may present squared or rectangular outer sections, typically intended to prevent the syringe from rolling on itself, e.g. when placed on a plane before or after its use. Generally, the known finger grip devices are an integral part of the cylindrical barrel, or alternatively, they can even be clipped to the afore mentioned flanges or outer sections. In addition, the finger-grip devices known in the art have also the function of locking and/or stopping the plunger during its run within the cylindrical barrel, in order for instance to avoid the accidental and inconvenient dropping out of the plunger from the body of the syringe.

US20030220615 describes a syringe having a finger-grip device allowing to stop the plunger during the operation of aspiration. This device is anchored to the cylinder by protuberances that penetrate inside the inner walls of the cylinder.

U.S. Pat. No. 5,997,514 describes a circular or elliptical shaped finger-grip device suitable for a cylindrical barrel of a syringe, or a cartridge, said device designed to be anchored outside the barrel, through a particular movement called "snap-on".

US2007083164 refers to an annular piece in the form of a ring to be assembled on the external surface of the barrel of a syringe. Said ring has an anti withdrawal effect so that once it is clipped to the syringe, it is impossible to withdraw the plunger from the syringe.

Similarly, U.S. Pat. No. 5,700,247 discloses a back-stop device to prevent the removal of the plunger from the syringe.

The finger-grip devices known in the art, however, have the disadvantage that special attention must be made in the placement of either the fingers or the hand of the operator in general, in particular to avoid the accidental disconnection or rotation on the device from or on the barrel respectively. In fact, in cases where the removal of the plunger from the barrel is needed for any reason, the finger grip has to be first disconnected to the syringe, and then replaced after the plunger has been re-inserted into the barrel, thus prolonging the operation time in general.

This operation in particular may pose some problem and limitation especially in cases of emergency, e.g. when the syringe, provided with the finger grip device, should be used in a short time frame due, for instance, to the patient's critical medical, or suddenly aggravated, conditions. Even further, when the device is anchored to the cylindrical barrel by flanges or means on the outside of the cylinder itself, the industrial production of such functionalised barrel, requires high precision technical passages, and in some cases, even complicated and specially optimized procedures.

We have now found that the disadvantages of the prior art can be overcome by using a finger-grip device, which can be anchored to the flange of the cylindrical barrel of a syringe, or a cartridge, in a secure and reliable way, thus providing an increased surface for the fingers, without hindering or stopping the plunger run.

SUMMARY OF THE INVENTION

Figure 1:
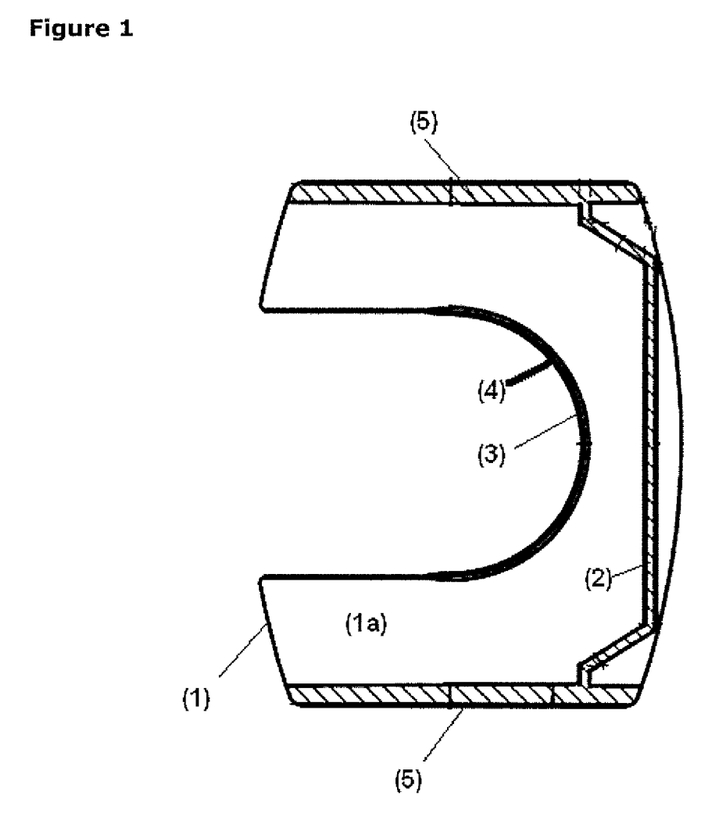
FIG. 1: bottom view of the bottom surface (1a) of the top part (1).
Figure 3:
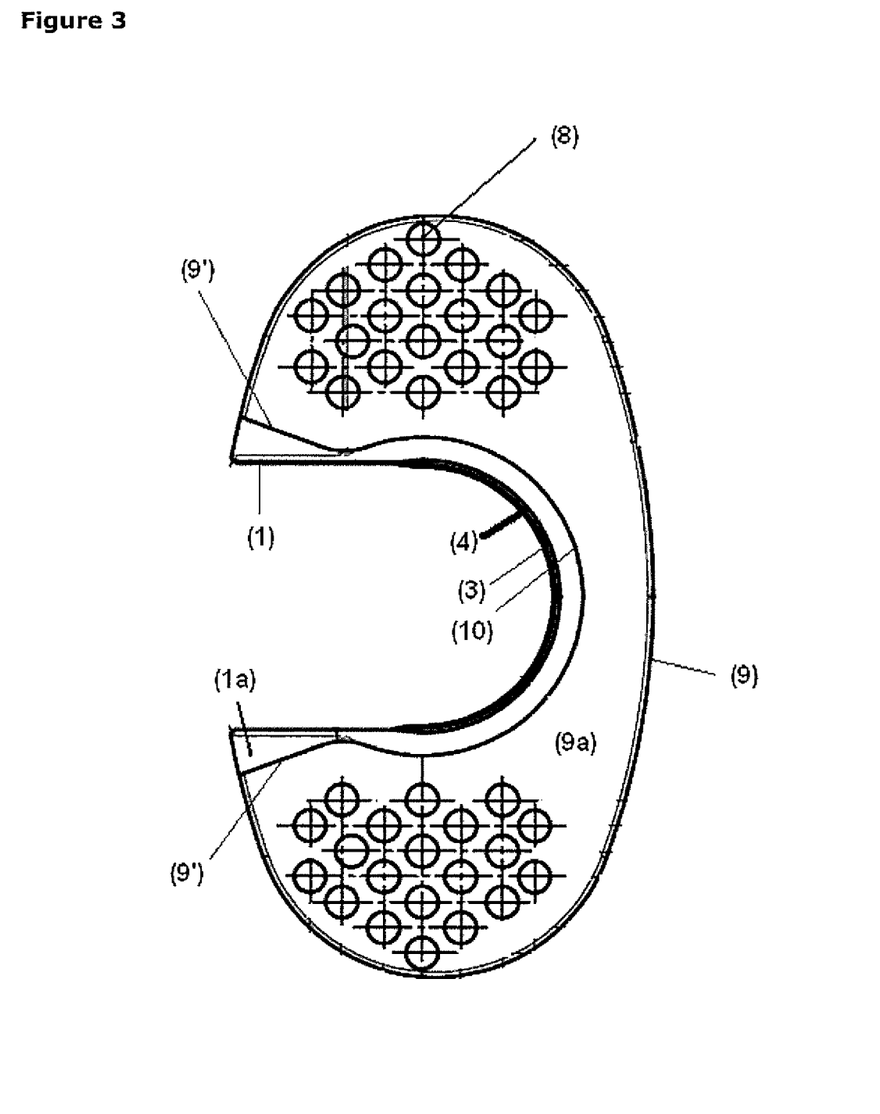
Figure 5:
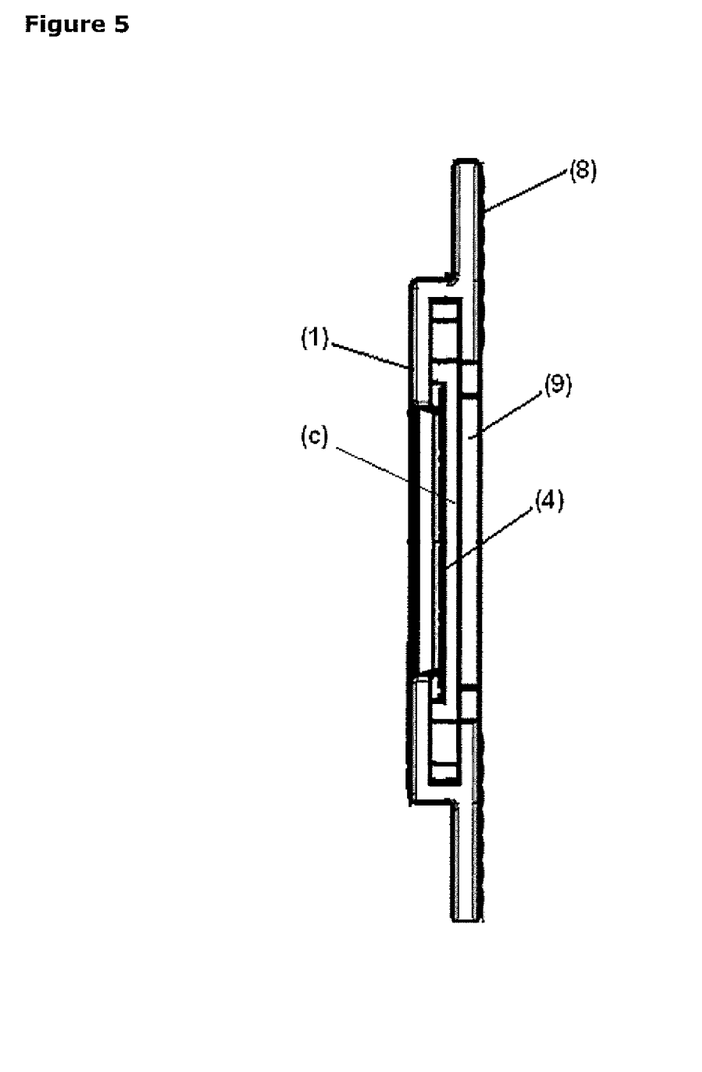

The present invention relates to a finger-grip device comprising:
a bottom part (9) (for example, as shown in FIG. 3) and
a top part (1) (for example, as shown in FIG. 1);
wherein said parties (9) and (1) have different sizes and are mutually connected one to each other to form a lodging area (c) (for example, as shown in FIG. 5) for the placement of the flange (12) of a cylindrical barrel of a syringe or cartridge, and wherein said top part (1) presents means (4) and (2) that allow the anchoring of the device to the flange (12) by a snapping and locking movement, said device characterised in that it does not block or hinder the run of the plunger within the barrel during injection or withdrawal operations.

The bottom part (9) and the top part (1) of the device can have various shapes, typically in order to facilitate the handle of the device by the operator, but also to facilitate the implementation of the device on an industrial scale process. Preferably the bottom part (9) has an open elliptical shape (FIG. 3), whereas the top part (1) as a pseudo-square open shape (see FIG. 1). Both parties (9) and (1) present coaxial circular open cavities, respectively (10) and (3), for the placement of the barrel, where the circular open cavity (10) has a diameter greater than the circular open cavity (3). Preferably, the cavity (10) has a diameter substantially equal to the outer diameter of the cylindrical barrel, while the cavity (3) has a diameter slightly lower than the inner diameter of the cylindrical barrel.

From the above it follows that the plunger run is not stopped or hindered during injection or withdrawal operations, once the finger grip device of the invention is anchored to the barrel.

Anti slip means (8), preferably in the form of high relief means can also be present on the lower surface (9a) of the bottom part (9) as indicated e.g. in FIG. 3.

Figure 6A:
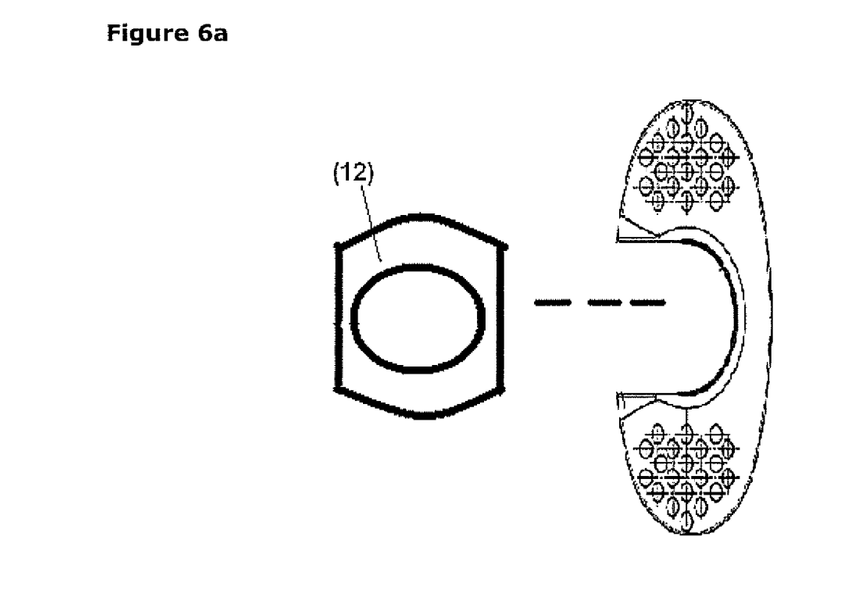
FIGS. 6a and 6b
Schematic representation of the possible directions of anchoring of the finger-grip device to the flange (12) of a cylindrical barrel.
Figure 6B:
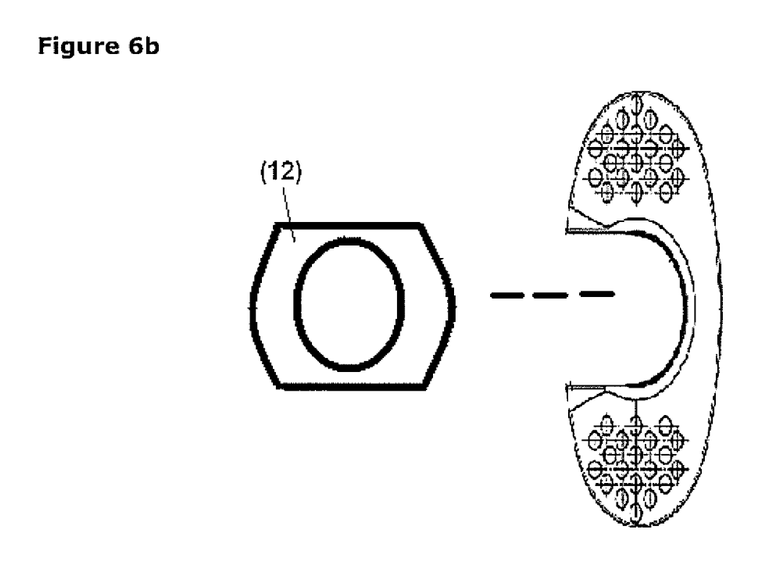

The device of the present invention can be conveniently anchored to the barrel of a medical syringe, or cartridge, by positioning the barrel flange (12) as illustrated in FIGS. 6a and 6b. Preferably the device is anchored to a pre-filled syringe, and even more preferably to a pre-filled syringe containing a contrast agent or medium.

According to a further aspect, the present invention relates to a kit of parts comprising the finger-grip device of the invention, in combination with a medical syringe, preferably a pre-filled syringe, even more preferably a prefilled syringe containing a contrast agent.

BRIEF DESCRIPTION OF THE DRAWINGS

FIGS. 1-6 represent schematically the finger-grip device of the present invention according to a preferred embodiment.

Description of the Figure (1) top part of the device, having a pseudo-square open shape.
(1a) bottom surface of the top part (1).
(2) continuous shaped rear edge that helps the lockage of the syringe by keeping the device firmly positioned with respect to the barrel.
(3) circular open cavity of the top part (1), with a diameter lower than 3 mm of the diameter of the cylindrical barrel of a syringe or cartridge.
(4) rear tab for the mechanical lockage of the barrel. Once the device is attached, (4) is positioned on the inner surface of the barrel.
(5) continuous solid border that joins the upper part (1) with the bottom of the device.

FIG. 3: bottom view of the finger-grip device.
(1) top part of the device having a pseudo-square open shape.
(1a) bottom surface of the top part of the device.
(4) rear tab for the mechanical lockage of the barrel. Once the device is attached, (4) is positioned on the inner surface of the barrel.
(8) anti-slip high relief means in the shape of spherical cap.
(9) bottom part of the device having elliptical open shape.
(9a) bottom surface of the bottom part presenting anti-slip high relief means (8).
(9') engagements or recesses to facilitate the locking to the cylindrical barrel of a syringe or cartridge.
(10) circular open cavity of the bottom part (9) with a diameter equal to the outer diameter of the barrel of the syringe or cartridge.

FIG. 4: Top view of the finger-grip device.
(1) top part of device having a pseudo-square open shape.
(1b) top surface of the top part.
(9) bottom part of the device having elliptical open shape.
(9b) top surface of the bottom part.
(4) rear tab for the mechanical lockage of the barrel. Once the device is attached, (4) is positioned on the inner surface of the barrel.

FIG. 5: Front view of the finger-grip device.
(1) top part of the device, having a pseudo-square open shape.
(4) rear tab for the mechanical lockage of the barrel. Once the device is attached, (4) is positioned on the inner surface of the barrel.
(8) anti-slip high relief means in the shape of spherical cap.
(9) bottom part of the device having elliptical open shape.
(c) lodging area: area formed between the bottom and the top part, configured to lodge the flange (12) of the cylindrical barrel of a syringe or cartridge.

DETAILED DESCRIPTION OF THE INVENTION

The present invention relates to an ergonomic finger-grip device which is applied to the flange of a cylindrical body of a syringe or a cartridge, providing improved contact surface with the fingers of the operator, typically with the index and the middle finger, thus facilitating the operations of injection or withdrawal of fluids, e.g. into or from a patient, without obstructing or blocking the run of the plunger within the barrel.

In more detail, the finger-grip device of the invention comprises:
a bottom part (9) (for example, as shown in FIG. 3) which preferably presents anti-slip means (8), and
a top part (1) (for example, as shown in FIG. 1);
wherein said parties (9) and (1) have different sizes and shapes and are joined one to each other, to form a lodging area (c) (for example, as shown in FIG. 5) for the flange (12) of a cylindrical barrel of a syringe or cartridge. As mentioned, the present finger grip device is characterised by the fact that it does not block or hinder the run of the plunger within the syringe or cartridge barrel, thus allowing the removal of the plunger from the syringe, even when the device is anchored on the cylindrical barrel.

The top part (1) presents means (4) and (2) that allow the anchoring of the device to the flange (12) through a "final-click snap-lock" movement.

The term "final-click snap-lock movement" or "snapping and locking movement" means a movement whereby the finger grip device is anchored to the barrel by firmly locking the flange of the barrel within the lodging area (c) until a click sound is heard.

Figure 4:
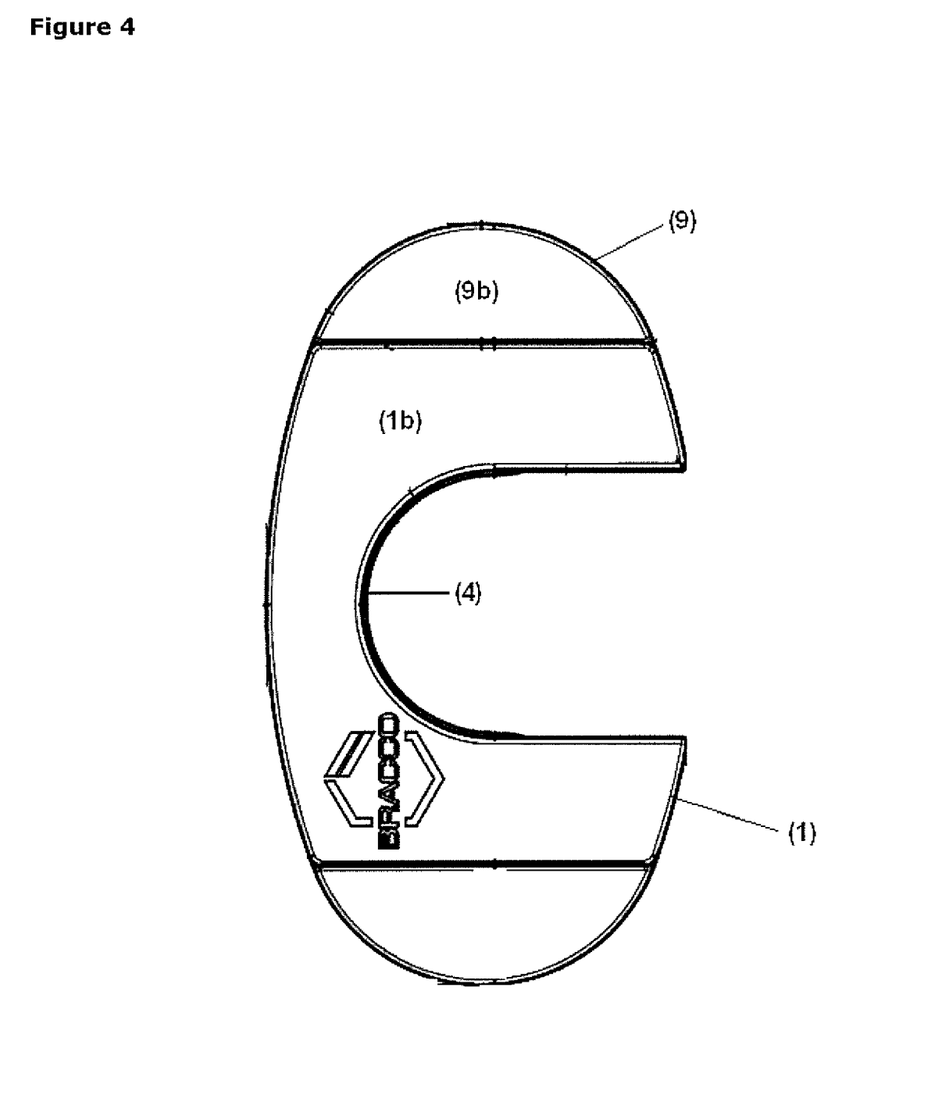

As shown in FIGS. 3 and 4, the bottom part (9) has preferably an elliptical open shape, whereas the top part (1) has preferably a pseudo-square open shape, whereby both parties presents coaxial circular open cavities (10) and (3), respectively (see FIG. 3).

The two parts (9) and (1) are joined to each other by a means (5) that may be, for example, an entirely profiled or discontinued edge, or it may be constituted by two or more points of connection, or similar. Preferably, the means (5) is an edge and more preferably is an entire profiled edge, for example as shown in FIG. 1.

Said means (5) in particular has dimensions such that the lodging area (c), that is formed between the parties (9) and (1), can effectively contain the flange of the barrel. Preferably, the edge (5) has a height corresponding to the distance between the outer edges of the flange (12) of a cylindrical body of a syringe or cartridge, and the lodging area (c) corresponds substantially to the surface of said flange.

The diameter of the two coaxial circular cavities (10) and (3) has values such that the anchoring of the finger-grip device of the invention to the cylindrical body of a syringe or cartridge is secure, reliable, and prevents the device to interfere with the run of the plunger, for example, by blocking the dropping out of the plunger from the cylinder, e.g. during withdrawal operations, or by limiting in general the run of the plunger during injection or withdrawal operations.

Thus, according to a preferred embodiment, the present invention relates to a finger-grip device comprising:
a bottom part (9) (for example, as shown in FIG. 3) having anti-slip high relief means (8), and
a top part (1) (for example, as shown in FIG. 1);
wherein said parties (9) and (1) have different sizes and are mutually connected one to each other to form a lodging area (c) (for example, as shown in FIG. 5) for the placement of the flange (12) of a cylindrical barrel of a syringe or cartridge, and wherein said top part (1) presents means (4) and (2) that allow the anchoring of the device to the flange (12) by a snapping and locking movement, said device characterised in that it does not block or hinder the run of the plunger during the injection or withdrawal of fluids.

In more detail, the two circular cavities (10) and (3) have preferably different diameters and, in particular, the circular cavity (10) has a diameter greater than the cavity (3). Preferably the diameter of the cavity (10) is comprised between about 12 mm and about 27 mm, and still more preferably it corresponds to the outer diameter of the cylindrical barrel of the syringe.

Accordingly, the circular cavity (3) has a diameter which is smaller no more than the 10% of the diameter of the cavity (10), preferably the diameter of the cavity (3) is lower than the diameter of (10) of a value comprised from 3 and 10%, more preferably, about 4-6%. According to a preferred embodiment of the invention, the diameter of the circular cavity (3) is comprised from about 10 mm and about 25 mm. In particular and as formerly indicated, the diameter of the circular cavity (3) is smaller than the inner diameter of the cylindrical barrel of a syringe, or cartridge, of a value such that the run of the plunger is not stopped or limited anyhow by the presence of the finger-grip device of the invention. Preferably, the diameter of the circular cavity (3) is lower than the inner diameter of the cylindrical barrel of a value comprised from 2 mm and 10 mm, more preferably from 4 mm and 6 mm.

In a still preferred embodiment, the diameter of the circular cavity (3) is lower than the inner diameter of the cylindrical barrel of a value comprised between 2 mm and 10 mm and lower than the cavity (10) diameter of a value comprised from about 4 and 6%.

For example, and according to a preferred embodiment, in a finger-grip device, for use with a cylindrical barrel having an inner diameter of 21.5 mm (such as a 20 ml syringe) the diameter of the cavity (3) should be 21.2 mm, whereas the diameter of the cavity (10) should correspond to 25.0 mm. Similarly, where the cylindrical barrel has an inner diameter of 10.7 mm (such as a 10 ml syringe), the diameter of (3) should be 10.5 mm, whereas the diameter of (10) should be equal to 12.4 mm.

In this way, the present device is characterised in that it allows the sliding of the plunger within the cylindrical body of the syringe in both directions (e.g. towards the terminal or the distal side), without limiting or stopping its run.

As shown in FIG. 3, the bottom part (9) of the finger-grip device of the invention presents recesses or engagements (9') intended e.g. to facilitate the attachment of the device to the cylindrical barrel of a syringe or cartridge. As mentioned above, the bottom part (9) of the device preferably presents a multiplicity of anti-slip means (8), even more preferably in the form of high relief means, intended to increase the grip with the operator's fingers, in the form, for example, of regions or areas with enhanced roughness, such as silicon spheres or grooves, that may have different shapes and sizes. "High relief means" means surface areas which extend perpendicularly to the base for at least 0.1 mm. Preferably said high relief means (8) are located on the bottom surface (9a) of the bottom part (9) of the present device, and they extend off said surface, preferably for about 0.2 to 0.5 mm.

The anti-slip means (8) can each other have the same shape or they can even present different shapes and/or sizes, generally selected from any three-dimensional geometric shape, such as: cube, prism, parallelepiped, regular or irregular, spherical, semi-spherical, spherical-cap, conical, truncated cone and the like. Such means (8) may also have segmented shapes, such as dotted lines or circular or semicircular lines or the like. Alternatively, the anti-slip means (8) are imprinted on the surface (9a) in the form or straight or shaped lines, either continuous or fragmented such as longitudinal dotted lines, or V-shaped lines and the like.

Figure 2:
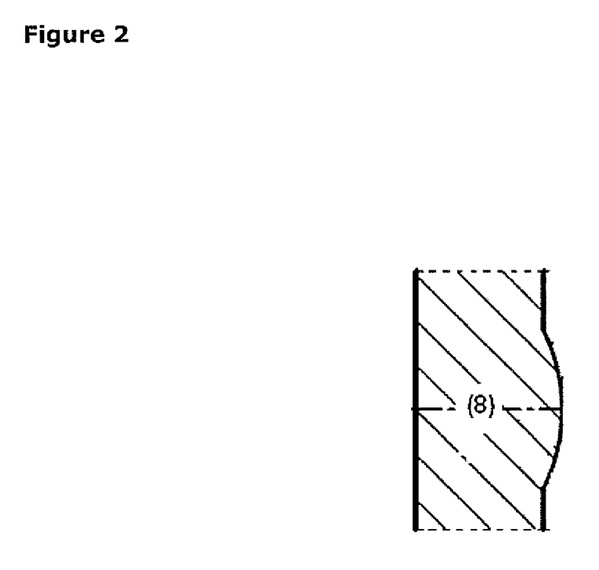
FIG. 2: side view of a anti-slip high relief means (8).

Preferably the means (8) are high relief means having a spherical-cap shape, as shown in FIGS. 2 and 3, and still more preferably, they are arranged to cover a portion or substantially the whole surface (9a) concerned. For example, and according to a further preferred embodiment, these means (8) are arranged in a regular and ordered manner, covering an area of at least about 10% of the lower surface (9a), preferably at least 50%, more preferably at least 80%. The diameter of the means (8) in the form of spherical-caps can vary between 1 mm and 5 mm, and consequently their number on the surface can vary from a few (e.g. 4 or more) up to a few tens (e.g. up to 60 or more). Preferably, the diameter of the means (8) in the form of spherical-caps is between about 2 mm and 3 mm and their number is between 20 and 60. The high relief means (8) may be of the same material as the finger grip device or can even be made with appropriate materials, such as silicon, polyester or the like. Typically, the means (8) are of the same material as the device itself.

In this regard, the finger-grip device of the present invention can be manufactured with a material that is at the same time rigid and flexible enough to be anchored to the syringe or cartridge without being cracked, chipped or damaged. Not limiting examples of suitable materials are: plastics such as polypropylene, medical polypropylene (medical PP), polyester, polycarbonate or the like. Generally, the device is made of a thermoplastic material, and is manufactured according e.g. to known industrial processes such as injection moulding or the like. Preferably the device is made of transparent medical polypropylene (medical PP).

As mentioned above, the finger-grip device of the invention comprises the means (4) and (2) having a shape and a height such that the anchoring of the device to the barrel occurs in a secure and stable manner, also preventing the device to freely rotate, e.g. around the flange of the cylindrical barrel, without interfering with the sliding of the plunger. Preferably, as shown for example in FIG. 1, the means (4) is a coaxial tab, suitably designed for the anchorage to the inner surface of the cylindrical barrel, whereas the rear part (2) is generally constituted by a shaped edge, either continuous or discontinuous. Preferably, the part (2) is a continuous board having the terminal portions suitably shaped as shown in FIG. 1.

As evident from the present description and as clearly indicated in the figures set forth, the present finger-grip device offers an improved and enhanced surface for the fingers of the operator, typically the index and middle finger, that whilst injecting, allows the operator to exert pressure on the plunger, typically with the thumb, in a safe and steady manner. The present device can be advantageously used both during injection and during withdrawal of fluids, providing in both cases not only a significant improvement in terms of handling of the syringe, but also a smooth and controlled sliding of the plunger, which, as said, can be conveniently removed from the barrel without disconnecting the device firstly.

In addition, the present device is easy to manufacture and to use, since its installation on the syringe does not requires any special technical knowledge or skills by the person who takes care of its assembly with the syringe.

In this regard, it should be noted that, the present device, as described above according to any preferred embodiments, can advantageously be applied to the flange of the cylindrical barrel of a syringe, or a cartridge, either longitudinal, i.e. as described in FIG. 6a, or latitudinal, that is, as shown in FIG. 6b, wherever said barrel presents squared or pseudo square flanges, such as the ones typically present on commercially pre-filled syringe for the administration of contrast agents, such as Multihance® or Prohance®. In both directions, in fact, the circular cavities (3) and (10) of the top and bottom parts respectively of the finger-grip device, do allow the anchoring of the device regardless of the direction of insertion of the flange (12). This feature is particularly advantageous especially in case of medical emergency, e.g. when the operator is in urgent situations that require a certain hurry and precision of execution at the same time.

In addition, the device of the present invention can be designed to be conveniently applied to the flange of syringes, or cartridges, for medical use, having different sizes and materials, ensuring in every case the results and benefits as formerly described. Typically the syringes, or cartridges, are commercially available products, having, a volume capacity comprised, for example, between 10 mL and 50 mL. These syringes or cartridges can be made, in whole or in part, for example of glass or plastic, or they may be of the same material as the finger-grip device. Preferably, they are made with a cyclic polyolefin resin.

The device of the invention is aimed to facilitate the use of syringes in general, but its use is clearly even more advantageous when applied to medical syringes containing high viscosity fluids (such as contrast media used in the diagnostic field and well known in the art), where a high pressure and force is required during the filling or emptying of the syringe barrel, and which are often present on the market as pre-filled syringes. As herein intended, "high-viscosity fluids" means liquids having a viscosity greater than 1 mPa at 20° C.

Unless otherwise provided, the term "agent" or "contrast agent" means any substance that can change the way in which a region is analyzed in a medical image. Examples of contrast agents known in the art and widely used for this purpose are: Iopamidol®, MultiHance®, ProHance® and the like.

In this regard, the present finger-grip device is preferably applied to syringes containing a fluid with a viscosity comprised between about 2 MPa to about 10 mPa, at 20° C. Such syringe may be a pre-filled syringe or it can be filled, in case with the aid of the present device, with the desired amount of chosen fluid, usually at the time of use.

Thus a further aspect of the invention refers to a syringe, preferably pre-filled syringe, comprising the finger grip device of the invention.

According to this further aspect, the syringe is preferably pre-filled with a fluid that can act as contrast agent in diagnostic experiments. In particular, according to a preferred further aspect of the invention, the present finger-grip device is applied to syringes pre-filled with MultiHance® or ProHance®. The finger-grip device of the invention can be anchored to the cylindrical barrel at the time of need, or it can be pre-assembled, or even packaged as additional component together with the syringe.

In more detail, according to a further aspect, the present invention relates to a kit of parts comprising:
the finger-grip device as described above; and
a medical syringe.

Said syringe is typically chosen e.g. from those described above. Preferably the present kit of parts includes the finger-grip device of the invention, and a pre-filled syringe, even more preferably pre-filled with a contrast medium, being MultiHance® even more preferred.

The finger-grip device can be packaged as a separate component or can be applied to the syringe and packaged together in the same kit of parts. If separated, the two components (i.e. the finger grip and the syringe or cartridge) can be housed in the kit of parts in the same compartment or into two different compartments. The present kit of parts can also include additional components such as, for example, needles, disinfectant swabs, sterile swabs and the like.

As extensively described above, the device of the present invention provides the operator with an increased and improved surface for the fingers, that allows an easy handling and safety action during the injection and withdrawal of fluids, together with a noticeable easiness of manufacturing and applicability. In particular, the device can be designed for an application to syringes and cartridges chosen, for example, among the common syringes used in medical and diagnostic techniques, either pre-filled or filled at the time of use.

Advantageously, the present device can be properly included in a kit of parts, together or separately to the syringe of choice, either already mounted on the same, or as additional component ready for the use.

The invention claimed is:

1. A finger-grip device for a syringe or cartridge with a barrel and a plunger comprising:
   a bottom part, and
   a top part;
   wherein said parts have different sizes and are mutually connected to each other to form a lodging area (c) for the placement on the flange of the cylindrical barrel of the syringe or cartridge, and wherein said top part presents means for anchoring of the device to the flange by a snapping and locking movement, said bottom part presents anti-slip means, and wherein the plunger and a plunger-rod can be removed from the barrel without disconnecting the device from the flange and without limiting a run of the plunger and plunger-rod within the barrel.

2. The device according to claim 1, wherein the bottom part has a first open shape, and the top part has a second open shape, and where both the parts have coaxial circular open cavities.

3. The device according to claim 1, wherein the circular open cavity in the top part has a diameter which is no more than 10% smaller than the diameter of the open cavity in the bottom part.

4. The device according to claim 3, wherein the diameter of the circular open cavity in the top part is no more than 3-10% smaller than the diameter of the cavity in the bottom part.

5. The device according to claim 3, wherein the diameter of the circular open cavity in the top part is no more than 4-6% smaller than the diameter of the open cavity in the bottom part.

6. The device according to any one of claim 1 or 3, wherein the diameter of the circular open cavity in the top part is smaller than the inner diameter of the cylindrical barrel of a syringe or cartridge by between 2 mm and 10 mm.

7. The device according to claim 1, wherein the diameter of the circular open cavity in the top part is 21.2 mm and the diameter of the circular open cavity in the bottom part is 25.0 mm.

8. The device according to claim 1, wherein the diameter of the circular open cavity in the top part is 10.5 mm and the diameter of the circular open cavity in the bottom part is 12.4 mm.

9. The device according to claim 1, wherein said anti slip means are in the form of high relief means.

10. The device according to claim 9, wherein said anti-slip high relief means have a spherical cap shape.

11. A syringe comprising the finger-grip device according to claim 1, anchored on the flange of said syringe.

12. The syringe according to claim 11, pre-filled with a contrast agent.

13. A kit of parts comprising the finger-grip device as defined in claim 1, in combination with a medical syringe or cartridge.

14. The kit according to claim 13, wherein said medical syringe is a contrast agent pre-filled medical syringe.

15. A finger-grip device for a syringe or cartridge with a barrel and a plunger comprising:
a bottom part, and
a top part;
wherein said parts have different sizes and are mutually connected to each other to form a lodging area (c) for the placement on the flange of the cylindrical barrel of the syringe or cartridge, and wherein said bottom part presents anti-slip means, and wherein the plunger and a plunger-rod can be removed from the barrel without disconnecting the device from the flange and without limiting a run of the plunger and plunger-rod within the barrel.

16. The device according to claim 15, wherein the bottom part has a first open shape, and the top part has a second open shape, and where both the parts have coaxial circular open cavities.

17. The device according to claim 15, wherein the diameter of the circular open cavity in the top part is no more than 3-10% smaller than the diameter of the cavity in the bottom part.

18. The device according to claim 15, wherein the diameter of the circular open cavity in the top part is smaller than the inner diameter of the cylindrical barrel of a syringe or cartridge by between 2 mm and 10 mm.

19. The device according to claim 15, wherein said anti slip means are in the form of high relief means.

\* \* \* \* \*